US011058838B2

(12) United States Patent
Grashow et al.

(10) Patent No.: US 11,058,838 B2
(45) Date of Patent: Jul. 13, 2021

(54) CUSTOMIZED MASK WITH RIGID SUPPORT

(71) Applicant: KONINKLIJKE PHILIPS N.V., Eindhoven (NL)

(72) Inventors: Jonathan Sayer Grashow, Eindhoven (NL); Lauren Patricia Chodkowski, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 128 days.

(21) Appl. No.: 16/061,883

(22) PCT Filed: Dec. 21, 2016

(86) PCT No.: PCT/EP2016/082212
§ 371 (c)(1),
(2) Date: Jun. 13, 2018

(87) PCT Pub. No.: WO2017/108974
PCT Pub. Date: Jun. 29, 2017

(65) Prior Publication Data
US 2018/0369529 A1    Dec. 27, 2018

Related U.S. Application Data

(60) Provisional application No. 62/270,812, filed on Dec. 22, 2015.

(51) Int. Cl.
*A61M 16/06* (2006.01)
*B29C 64/386* (2017.01)
*B33Y 80/00* (2015.01)

(52) U.S. Cl.
CPC ........ *A61M 16/06* (2013.01); *A61M 16/0605* (2014.02); *B29C 64/386* (2017.08);
(Continued)

(58) Field of Classification Search
CPC .......... A61M 2016/0661; A61M 16/06; A61M 16/0605; A61M 16/0611; A61M 16/0616;
(Continued)

(56) References Cited

U.S. PATENT DOCUMENTS

| | | | |
|---|---|---|---|
| 6,728,589 B1 * | 4/2004 | Delache | A61M 16/06 128/206.21 |
| 9,352,113 B2 | 5/2016 | Deguilio | |

(Continued)

FOREIGN PATENT DOCUMENTS

| | | |
|---|---|---|
| EP | 1116492 A2 | 7/2001 |
| WO | 2011049548 A1 | 4/2011 |

(Continued)

*Primary Examiner* — Joseph D. Boecker
(74) *Attorney, Agent, or Firm* — Michael W. Haas (57) ABSTRACT

A customized mask is manufactured by the process of: generating surface geometry data of a face of a patient, the surface geometry data corresponding to and representing a surface geometry of the face of the patient; generating original cushion geometry data using the surface geometry data; generating modified cushion geometry data using the original cushion geometry data; producing a rigid support member using the modified cushion geometry data such that it is shaped according to the modified cushion geometry data, the support member being made of a unitary material; and coupling a sealing flap to the support member, the sealing flap being structured to engage the face of the patient.

4 Claims, 8 Drawing Sheets

(52) U.S. Cl.
CPC . *A61M 2016/0661* (2013.01); *A61M 2207/00* (2013.01); *A61M 2207/10* (2013.01); *B33Y 80/00* (2014.12)

(58) Field of Classification Search
CPC .......... A61M 16/0622; A61M 16/0683; A61M 16/08; A61M 16/0816; A61M 16/0875; A61M 2207/00; A61M 2207/10
See application file for complete search history.

(56) References Cited

U.S. PATENT DOCUMENTS

| | | | |
|---|---|---|---|
| 9,881,426 B2 | 1/2018 | Van Bree et al. | |
| 2007/0215161 A1 | 9/2007 | Frater | |
| 2008/0006273 A1 | 1/2008 | Thornton | |
| 2009/0267261 A1* | 10/2009 | Mark | A61M 16/06 264/222 |
| 2010/0313891 A1 | 12/2010 | Veliss | |
| 2012/0305003 A1* | 12/2012 | Mark | A61M 16/06 128/206.24 |
| 2014/0261430 A1 | 9/2014 | Davis | |
| 2014/0326243 A1* | 11/2014 | Znamenskiy | A61M 16/0633 128/205.25 |
| 2015/0075533 A1 | 3/2015 | Howard | |
| 2015/0265794 A1* | 9/2015 | De Kruyff | A61M 16/06 128/200.23 |
| 2015/0273170 A1* | 10/2015 | Bachelder | A61M 16/0605 128/205.25 |
| 2017/0182273 A1 | 6/2017 | Ho | |
| 2018/0369530 A1* | 12/2018 | Chodkowski | A61B 5/0064 |
| 2019/0232013 A1* | 8/2019 | Yu | A61M 16/0683 |

FOREIGN PATENT DOCUMENTS

| | | | |
|---|---|---|---|
| WO | 2014024086 A1 | 2/2014 | |
| WO | 2014091370 A1 | 6/2014 | |
| WO | WO-2014091370 A1 * | 6/2014 | ........ A61M 16/0622 |
| WO | 2014150739 A1 | 9/2014 | |
| WO | 2015009172 A1 | 1/2015 | |

* cited by examiner

CUSTOMIZED MASK WITH RIGID SUPPORT

CROSS-REFERENCE TO RELATED APPLICATIONS

This patent application claims the priority benefit under 35 U.S.C. § 371 of international patent application no. PCT/IB2016/082212, filed Dec. 21, 2016, which claims the priority benefit under 35 U.S.C. § 119(e) of U.S. Provisional Application No. 62/270,812 filed on Dec. 22, 2015, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and in particular to customized masks for patient interface devices. The present invention further relates to methods of manufacturing customized masks.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping. Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional masks include a sealing feature and a support feature that is connected to the sealing feature. The sealing feature is typically very thin and has minimal intrinsic strength to allow it to conform to the face of the patient without significantly impacting the face of the patient. The support feature compresses the face to create a robust seal and to mechanically couple the mask to the face to prevent the mask from moving throughout the night. The support feature, unlike the sealing feature, imparts relatively large compressive forces onto the face of the patient. In existing masks, both the support feature and the sealing features are made from soft materials (e.g., silicone, rubber, gel, and foam). In order to manufacture a customized mask, the customized support features typically require custom molding techniques, which are time consuming, and relatively expensive and inaccurate.

SUMMARY OF THE INVENTION

Accordingly, it is an object of the present invention to provide a customized mask and a method of manufacturing a customized mask. The steps to manufacture the customized mask include generating surface geometry data of a face of a patient, the surface geometry data corresponding to and representing a surface geometry of the face of the patient; generating original cushion geometry data using the surface geometry data, the original cushion geometry data having first data representing a first facial portion and second data representing a first base portion extending from the first facial portion, the first facial portion having a number of regions and being shaped to match the surface geometry of the patient as represented by the surface geometry data; generating modified cushion geometry data using the original cushion geometry data, the modified cushion geometry data having third data representing a second facial portion and fourth data representing a second base portion, wherein the second facial portion is shaped differently than the first facial portion by changing portions of the first data corresponding to at least one of the regions of the first facial portion; producing a rigid support member using the modified cushion geometry data such that it is shaped according to the modified cushion geometry data, the support member being made of a unitary material; and coupling a sealing flap to the support member, the sealing flap being structured to engage the face of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the term "geometry" shall mean a three-dimensional profile of a surface or object. As used herein, the term "unitary" shall mean a homogeneous material having constant material properties throughout. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the term "three-dimensional scanner" shall mean a device that analyzes a real-world object and generates data (e.g., digital data) that represents the shape of the object in three dimensions, and shall include, without limitation, contact scanners that probe the subject through physical touch to generate the shape data, non-contact active scanners that emit some kind of radiation or light and detect its reflection or passing through the object to generate the shape data, and non-contact passive scanners that detect reflected ambient radiation to generate the shape data.

As employed herein, the term "rendering" shall mean an image generated from two-dimensional or three-dimensional data that represents the shape of the object.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
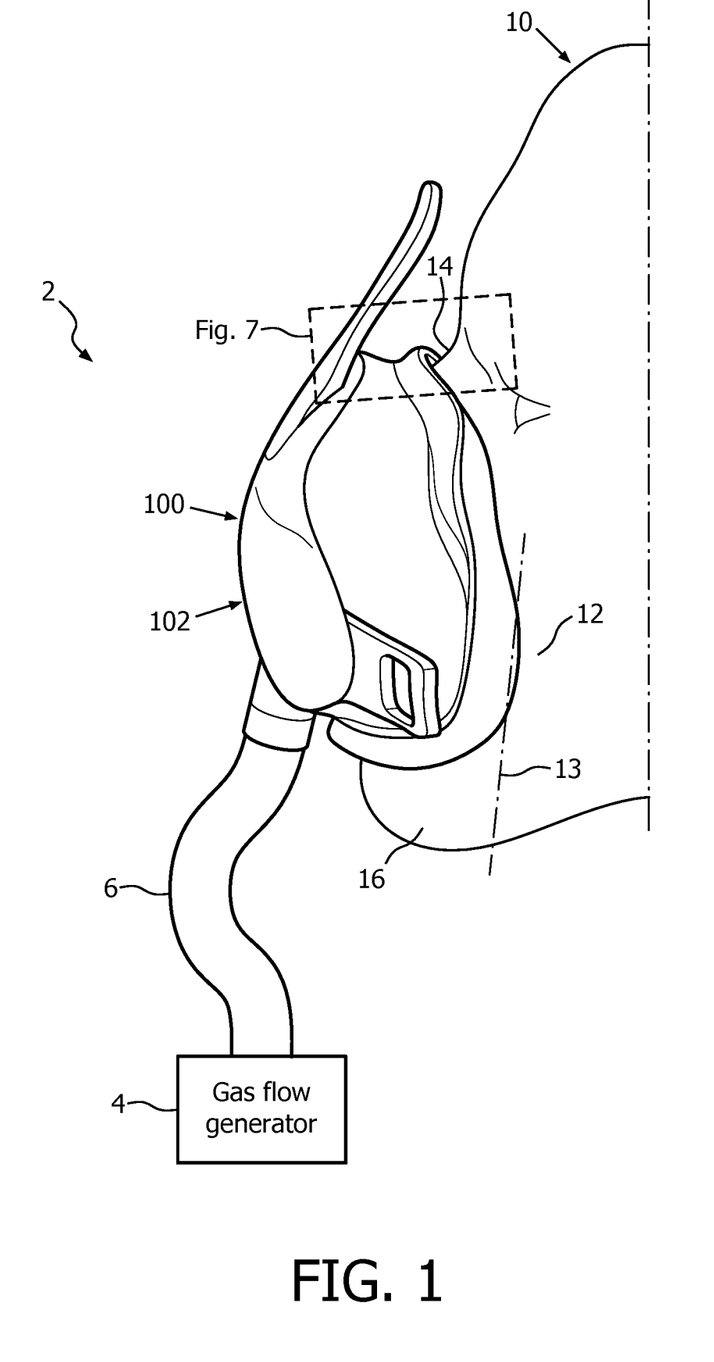
FIG. 1 is a simplified view of a pressure support system including a customized mask, shown as employed on a patient, in accordance with a non-limiting embodiment of the disclosed concept.
Figure 2:
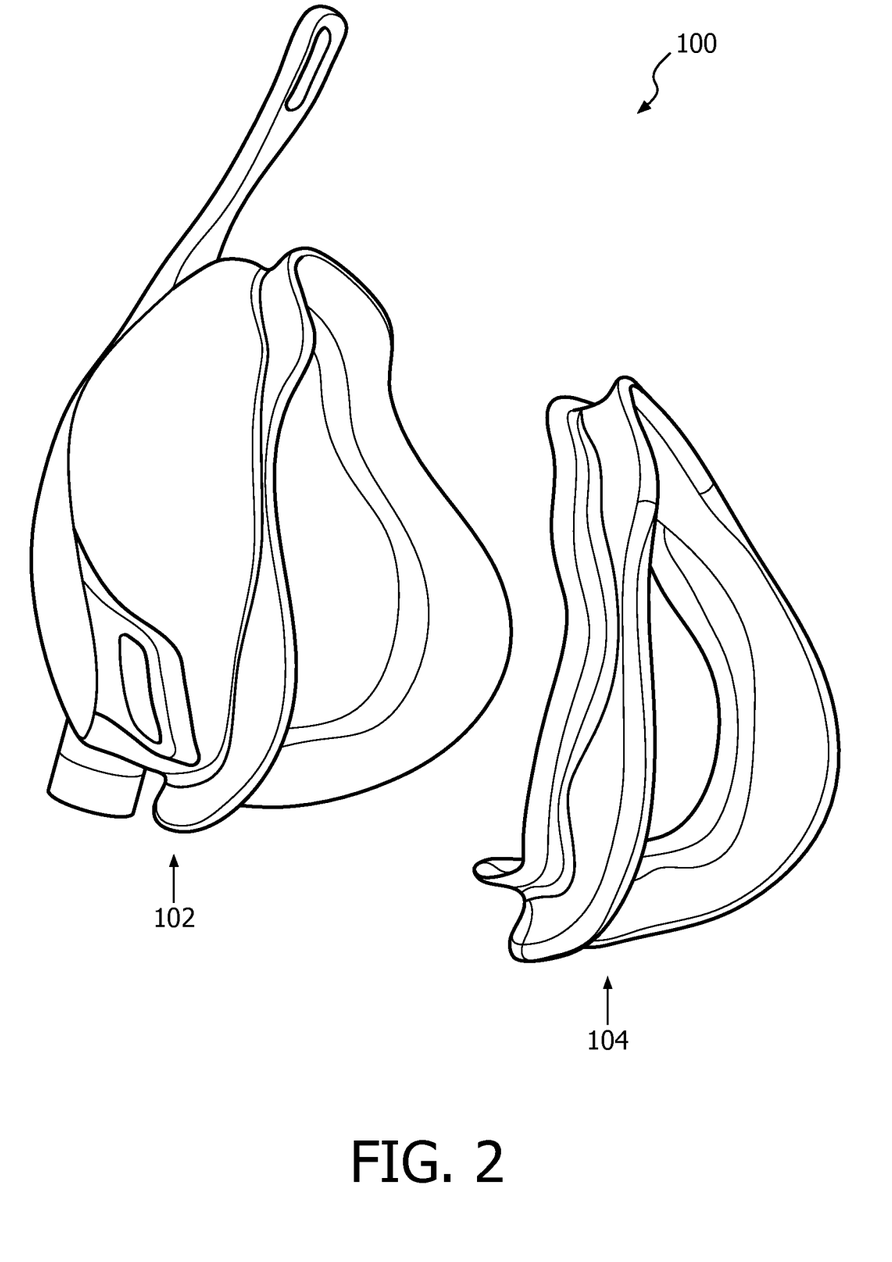
FIG. 2 is an exploded view of the customized mask for the pressure support system of FIG. 1.

FIG. 1 shows a pressure support system 2 in accordance with a non-limiting embodiment of the disclosed concept. Pressure support system 2 includes a gas flow generator 4, a gas delivery conduit (e.g., hose 6), and a customized mask 100. Hose 6 fluidly couples gas flow generator 4 to customized mask 100 in order to communicate a flow of breathing gas to a patient 10. As shown in FIG. 2, customized mask 100 includes a rigid support member 102 and a sealing flap 104 structured to be coupled to support member 102. Sealing flap 104 is structured to engage the face of patient 10. Support member 102 is made of a unitary material. For example and without limitation, in the exemplary embodiment, support member 102 has a constant modulus of elasticity throughout that is between 400 and 3,000 megapascals. That is, if a given location of support member 102 has a modulus of elasticity of 1,000 megapascals (e.g., or any other modulus of elasticity of between 400 and 3,000 megapascals), every other location of support member 102 has the same modulus of elasticity (i.e., in the case of 1,000 megapascals, every other location of support member 102 has a modulus of elasticity of 1,000 megapascals). Typical prior art customized support members are softer and have moduli of elasticity of between 10 and 100 megapascals. Accordingly, because support member 102 is more stiff than prior art custom support members, more reliable methods of manufacture may be employed, which yield novel advantages, as will be discussed in greater detail hereinbelow.

Customized mask 100 is advantageously structured to be employed in pressure support system 2 without causing undesirable discomfort to patient 10. More specifically, patient 10 has two cheek regions (e.g., only one cheek region 12 is depicted in FIG. 1), a nose bridge region 14, and a chin region 16. Cheek regions 12 are less stiff than nose bridge region 14 and chin region 16 due to the bony structures underneath the skin in nose bridge region 14 and chin region 16. Customized mask 100 is structured to compress (i.e., displace) relatively soft cheek regions 12 more than relatively stiff nose bridge region 14 and chin region 16 such that the contact pressure (i.e., force per unit surface area) is in a relatively comfortable range for all regions of the face of patient.

Figure 3:
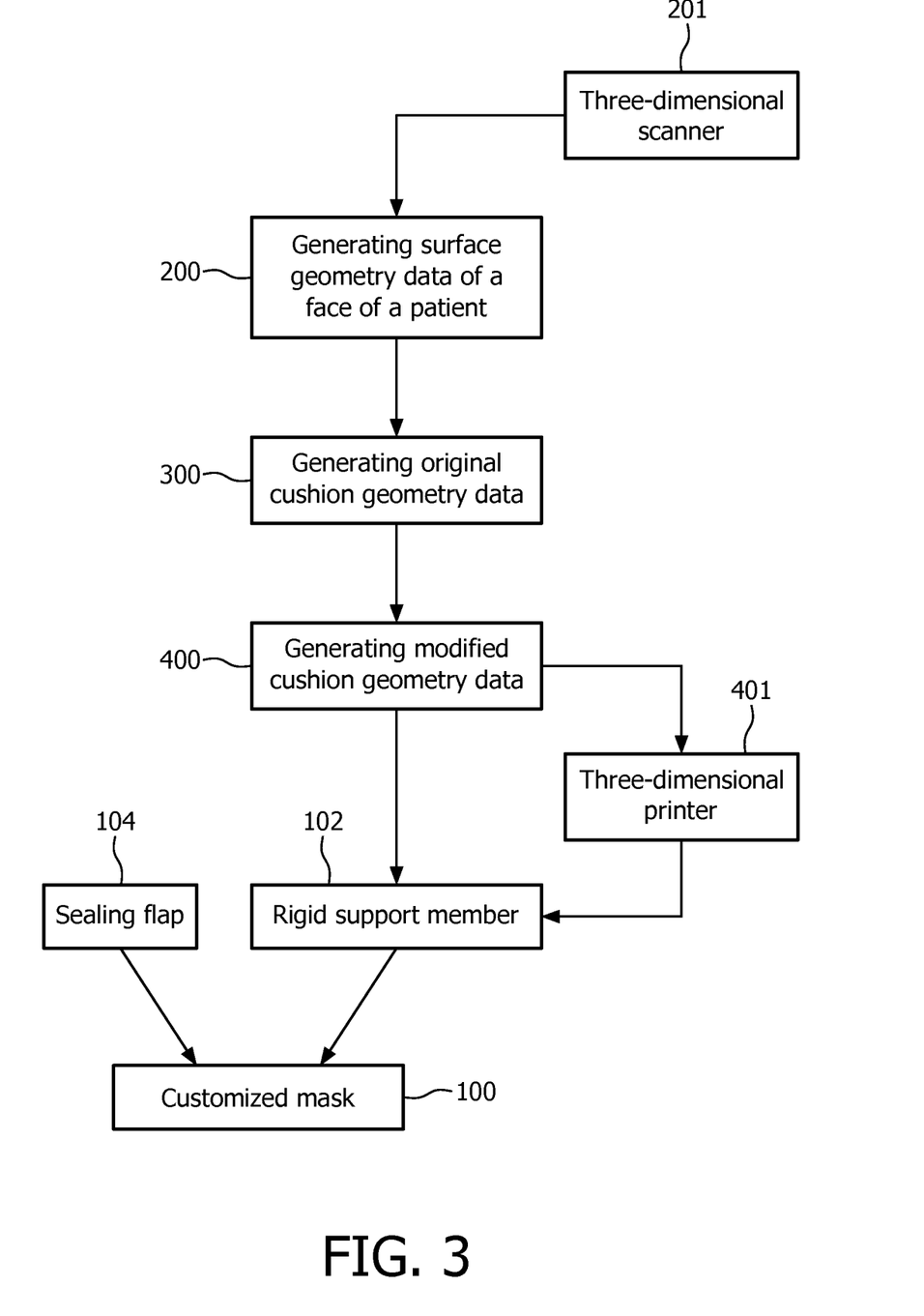
FIG. 3 is a schematic diagram, in block form, of a manufacturing process for the customized mask of FIG. 1.
Figure 4:
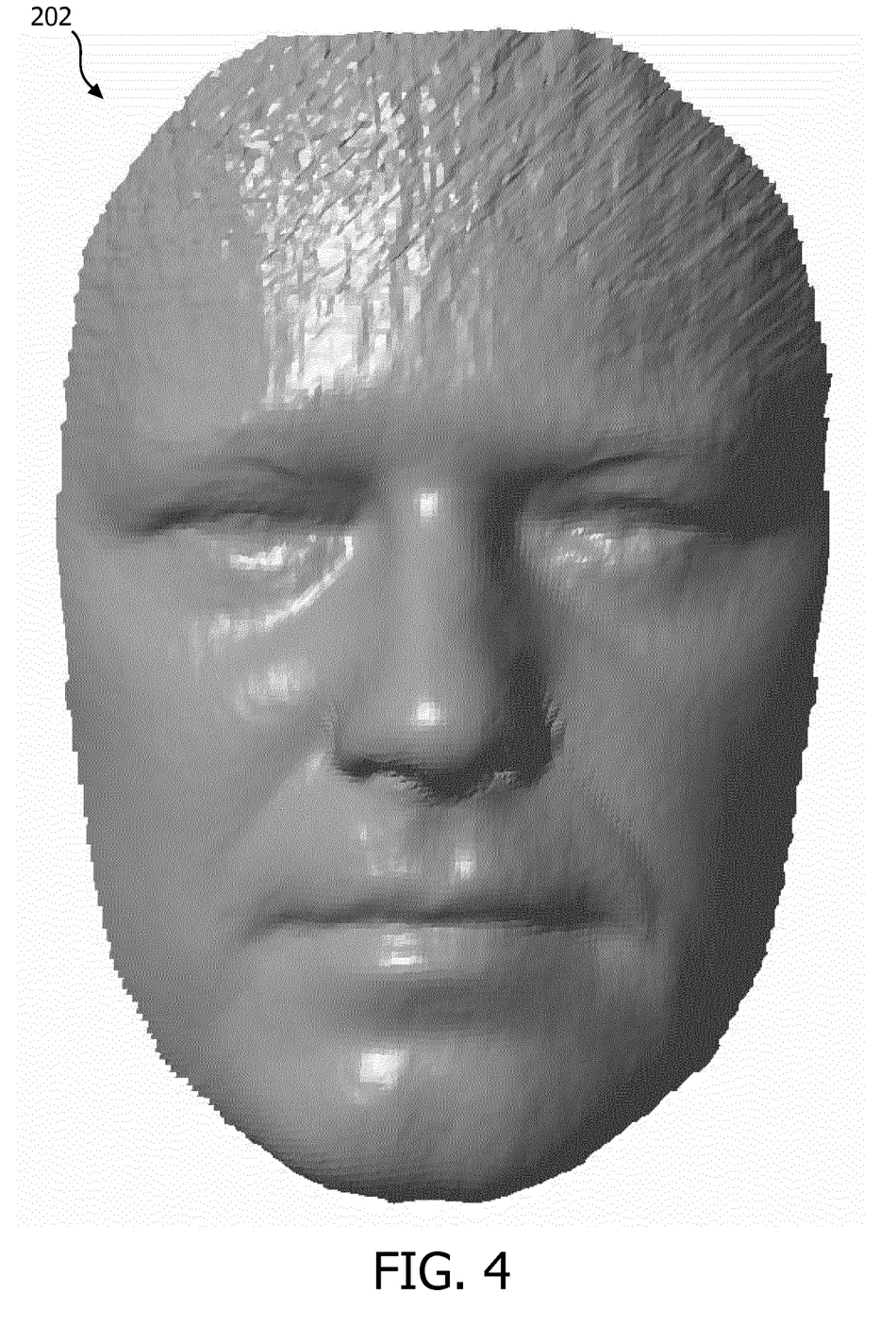
FIG. 4 is a top plan view of a rendering corresponding to surface geometry data of a face of the patient.

FIG. 3 shows a schematic diagram, in block form, of a process to manufacture customized mask 100. The first step 200 is generating surface geometry data that corresponds to and represents a surface geometry of the face of patient 10. In one exemplary embodiment, the generating step 200 includes scanning the face of patient 10 with a three-dimensional scanner 201 to generate the surface geometry data. It will be appreciated that other suitable alternative methods of generating surface geometry data may also be employed without departing from the scope of the disclosed concept. An example rendering 202 corresponding to the surface geometry data generated in step 200 on, for example, a computer screen, is shown in FIG. 4. The next step 300 is generating original cushion geometry data using the surface geometry data generated in step 200. The original cushion geometry data represents the three-dimensional shape of a predetermined cushion type (e.g., full face, nasal, cradle style) that includes as a part thereof a facial portion shaped to match and coincide with the surface geometry of patient 10 as represented by the surface geometry data generated in step 200.

Figure 5:
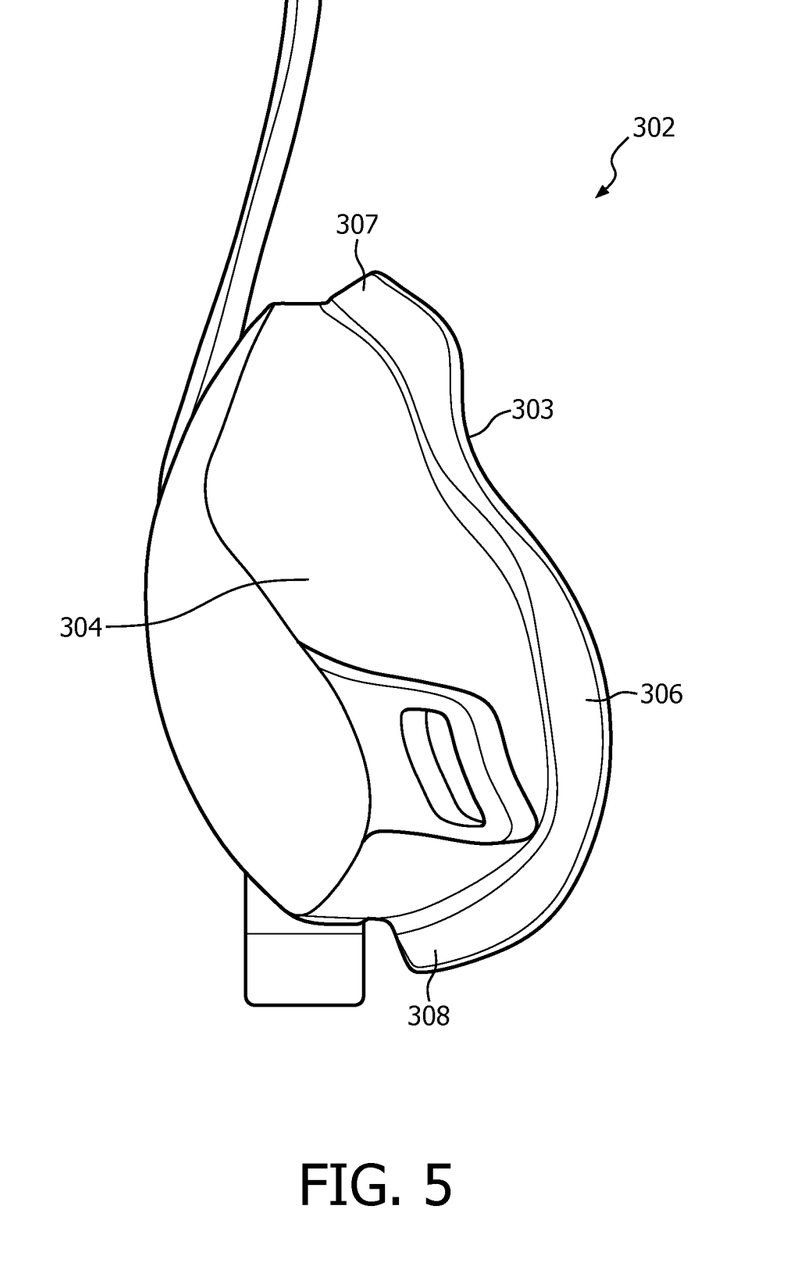
FIG. 5 is a side elevation view of a rendering corresponding to original cushion geometry data.

An example rendering 302 corresponding to the original cushion geometry data generated in step 300 as shown on, for example, a computer screen, is shown in FIG. 5. The original cushion geometry data corresponding to rendering 302 has data representing a facial portion 303 and data representing a base portion 304 extending from facial portion 303. In the depicted exemplary embodiment, rendering 302 is for a full face mask. As a result, facial portion 303 is annular-shaped and is for surrounding the nose and the mouth of patient 10. Facial portion 303 is also shaped to match and coincide with rendering 202. That is, facial portion 303 has the same profile as (i.e., overlaps with, corresponds to) rendering 202 such that if facial portion 303 is applied to (i.e., introduced on top of) rendering 202, there would be no gaps between rendering 202 and facial portion 303, and there would be no extensions of facial portion 303 into rendering 202. In other words, the portions of rendering 202 and facial portion 303 that correspond to one another (i.e., respective nose, cheek, and chin areas of rendering 202 and facial portion 303) have a contour or a shape that is exactly the same. As shown, facial portion 303 includes a number of regions 306,307,308.

Figure 6:
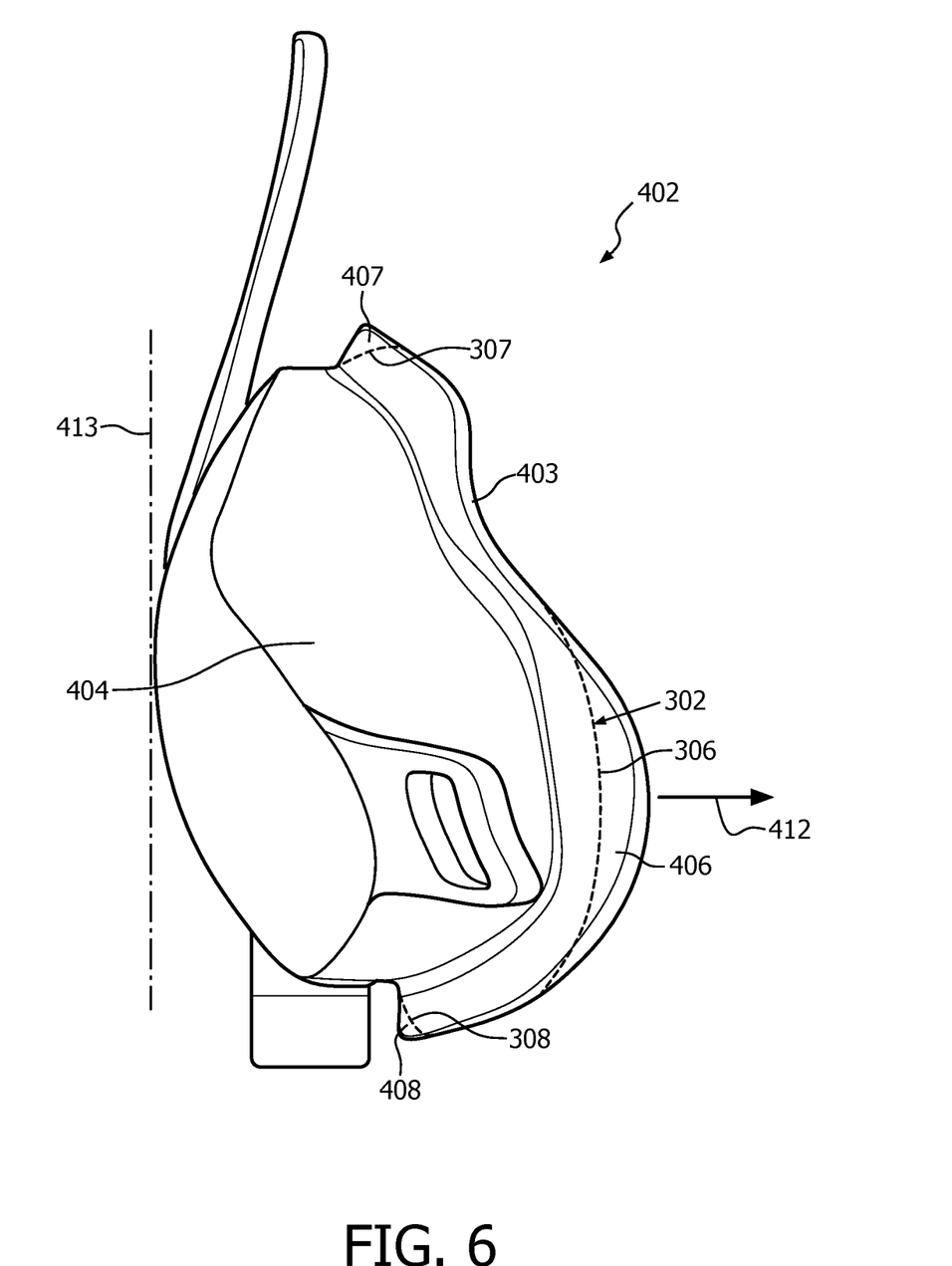
FIG. 6 is a side elevation view of a rendering corresponding to modified cushion geometry data.

Referring again to FIG. 3, the manufacturing method further includes the step 400 of generating modified cushion geometry data using the original cushion geometry data generated in step 300. An example rendering 402 corresponding to the modified cushion geometry data generated in step 400 as shown on, for example, a computer screen, is shown in FIG. 6. As seen, rendering 402 is shaped differently than rendering 302 (e.g., rendering 302 is partially introduced in FIG. 6 in dashed line drawing). The modified cushion geometry data has data representing a facial portion 403 and data representing a base portion 404 extending from facial portion 403. Facial portion 403 has a number of regions 406,407,408. Facial portion 403 is shaped differently than facial portion 303 (FIG. 5) by changing portions of the data corresponding to at least one of regions 306,307, 308 of facial portion 303.

More specifically, the step 400 further includes employing a predetermined algorithm to change the portions of the data representing facial portion 303. The algorithm is based on known information of tissue depth/hardness of a face of a typical patient. However, in a suitable alternative embodiment, the algorithm may also be based on customized tissue depth/hardness information for patient 10. By inputting data corresponding to contact locations between facial portion 303 and a surface geometry of patient 10 (e.g., locations where facial portion 303 and rendering 202 coincide) into the algorithm, the modified cushion geometry data can be generated. It will be appreciated that a different algorithm may be employed for each different mask-type. For example, a full face algorithm may be employed for full face customized mask 100, and a different algorithm may be employed for a cradle style mask. It will also be appreciated that other suitable alternative methods of changing the portions of the data representing facial portion 303 may be employed without departing from the scope of the disclosed concept.

The data representing facial portion 303 has data representing regions 306,307,308, and the data representing facial portion 403 has data representing regions 406,407,408. The step 400 (FIG. 3) further includes generating the data representing region 406 (i.e., the cheek regions) using the data representing region 306 (i.e., the cheek regions) such that region 306 is extended outwardly from base portion 304 to form region 406. As shown, region 306 is extended in a direction 412 to form region 406. Direction 412 may, without limitation, be a direction perpendicular to a surface plane 13 (FIG. 1) of cheek region 12 and into the face of patient 10. Direction 412 may also, without limitation, be a direction perpendicular to a frontal face plane 413 of patient 10 (plane 413 is shown in FIG. 6 for purposes of illustration due to the side elevation orientation of rendering 402) and into the face of patient 10, due to the direction by which customized mask 100 is pulled onto patient 10. Additionally, the step 400 (FIG. 3) further includes generating the data representing regions 407 (i.e., the nose bridge region), 408 (i.e., the chin region) using the data representing regions 307,308, respectively, such that the regions 307,308 are extended outwardly with respect to an interior of base portion 304 to form regions 407,408, respectively.

Referring again to FIG. 3, the next step is producing rigid support member 102 using the modified cushion geometry data generated in step 400 such that it is shaped according to the modified cushion geometry data. In one exemplary embodiment, the producing step includes printing support member 102 with a three-dimensional printer 401 based on the modified cushion geometry data. It will be appreciated that other suitable alternative producing methods (e.g., without limitation, employing a computer numerical control machine to produce the rigid support member by removing unwanted material from a piece of stock material) may be employed without departing from the scope of the disclosed concept. The next step is coupling sealing flap 104 to support member 102.

Figure 7:
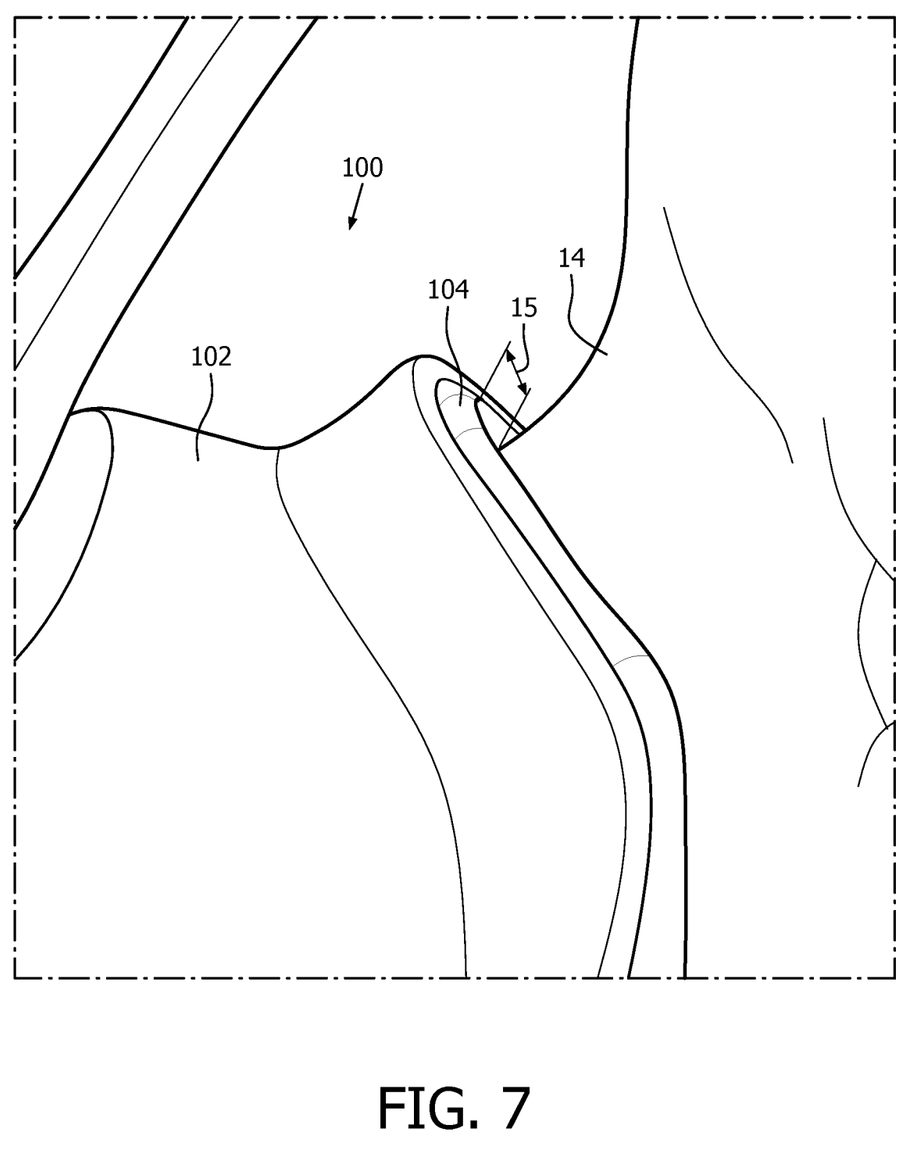
FIG. 7 is an enlarged view of a portion of the customized mask of FIG. 1, shown as employed on the patient.

It will be appreciated that support member 102, which is shaped according to (i.e., has a shape corresponding directly to or without deviation from) the modified cushion geometry data, is advantageously structured to compress (i.e., displace) relatively soft cheek regions 12 more than relatively stiff nose bridge region 14 and chin region 16. To illustrate, reference is made to FIG. 7, which shows an enlarged view of a portion of FIG. 1. As shown, sealing flap 104 and support member 102 are spaced a distance 15 from a portion of nose bridge region 14. It will similarly be appreciated that sealing flap 104 and support member 102 are spaced a distance from a portion of chin region 16 of patient 10.

This is distinct from typical prior art customized mask constructions, in which the facial geometry of the mask is structured to correspond exactly to the geometry of the face of the patient, a construction that would result in undesirable discomfort and/or pain to a patient if the mask were made of rigid materials having moduli of elasticity similar to that of support member 102. Additionally, sealing flap 104 and support member 102, due to the modification of the data corresponding to regions 306 to generate the data corresponding to regions 406, is structured to compress (i.e., displace) relatively soft cheek regions 12 more than relatively stiff nose bridge region 14 and chin region 16. That is, as compared to a similar mask having cheek regions shaped the same as the cheek regions of the face of the patient, customized mask 100, with extended regions proximate cheek regions 12 of patient 10, displaces cheek regions 12 a greater distance when donned by patient 10. Because the underlying tissue of cheek regions 12 is relatively soft (i.e., softer than the bony tissue underlying nose bridge region 14 and chin region 16), the potential for undesirable discomfort as a result of support member 102 being shaped according to the modified cushion geometry data is significantly minimized.

Moreover, because support member 102 is able to be made of rigid materials instead of traditional soft materials (i.e., as a result of using the modified cushion geometry data instead of the original cushion geometry data), employing three-dimensional printer 401 (FIG. 3) provides advantages in terms of accuracy, durability, biocompatibility (e.g., without limitation, by employing resins as the printing material), cost, speed, and/or number of available materials. Additionally, employing three-dimensional printer 401 (FIG. 3) allows engineering thermoplastics (e.g., without limitation, polycarbonates) to be printed.

Figure 8:
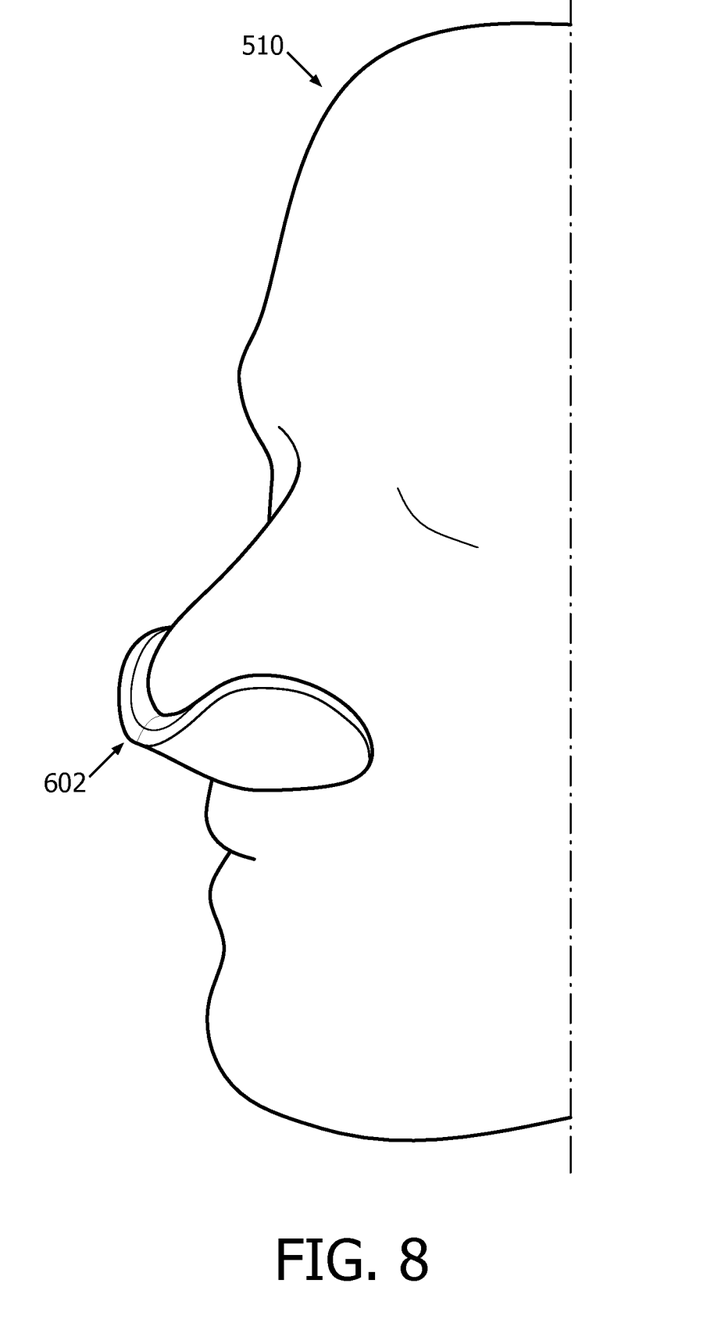
FIG. 8 is a simplified view of another rigid support member, shown as employed on a patient, in accordance with another non-limiting embodiment of the disclosed concept.

FIG. 8 shows a simplified view of a rigid support member 602 as employed on a patient 510, in accordance with another non-limiting embodiment of the disclosed concept. It will be appreciated that support member 602 is a simplified view of the general shape of a cradle style support member. Support member 602 is made by a similar process as support member 102, discussed above. That is, support member 602 is shaped according to modified cushion geometry data that is based on, but is different from (i.e., modified due to the stiffness of one region of the nose of patient 510 relative to another region of the nose of patient 510) original cushion geometry data. Because the septum area of the nose of patient 510 is more stiff than the relatively soft outermost regions of the nostrils, support member 602 is structured to compress (i.e., displace) the relatively soft outermost regions of the nostrils of patient 510 more than the relatively stiff septum area of the nose of patient 510, much like support member 102 is structured to compress (i.e., displace) relatively soft cheek regions 12 more than relatively stiff nose bridge region 14 and chin region 16. Accordingly, advantages associated with customized mask 100 apply to a customized mask including support member 602, which is made by a similar process and is made of a unitary material having the same material properties as support member 102. Furthermore, it will be appreciated that the disclosed method may be employed to manufacture a suitable alternative customized mask (e.g., without limitation, customized masks including pillows style support portions), without departing from the scope of the disclosed concept.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of manufacturing a customized mask comprising the steps of:
    generating surface geometry data of a face of a patient, the surface geometry data corresponding to and representing a surface geometry of the face of the patient;
    generating original cushion geometry data using the surface geometry data, the original cushion geometry data having first facial portion data representing a first facial portion and first base portion data representing a first base portion extending from the first facial portion, the first facial portion having a plurality of regions and being shaped to match the surface geometry of the patient as represented by the surface geometry data, the plurality of regions including a cheek region and a nose bridge region, the first facial portion data representing a first cheek region and a first nose bridge region;
    generating modified cushion geometry data using the original cushion geometry data, the modified cushion geometry data having second facial portion data representing a second facial portion and second base portion data representing a second base portion that matches the first base portion, wherein the second facial portion is shaped differently than the first facial portion by changing portions of the first facial portion data corresponding to the plurality of regions of the first facial portion;
    producing a rigid support member using the modified cushion geometry data such that it is shaped according to the modified cushion geometry data, the support member being made of a unitary material; and
    coupling a sealing flap to the support member, the sealing flap being structured to engage the face of the patient,
    wherein the first facial portion data has first cheek region data representing the first cheek region and first nose bridge region data representing the first nose bridge region,
    wherein the second facial portion data has modified cheek region data representing a modified cheek region and modified nose bridge region data representing a modified nose bridge region,
    wherein the modified cheek region data is generated using the first cheek region data such that the modified cheek region extends further outwardly into the face of the patient from the second base portion than the first cheek region extends from the first base portion, and wherein the modified nose bridge region data is generated using the first nose bridge region data such that the modified nose bridge region extends further outwardly from the second base portion than the first nose bridge region extends from the first base portion.

2. The method according to claim 1, wherein the producing step further comprises: printing the support member with a three-dimensional printer.

3. The method according to claim 1, wherein the support member has a constant modulus of elasticity.

4. The method according to claim 1, wherein the support member has a modulus of elasticity between 400 and 3,000 megapascals.

* * * * *